United States Patent [19]

Stack et al.

[11] Patent Number: 4,748,240

[45] Date of Patent: May 31, 1988

[54] PSYCHOTROPIC BICYCLIC IMIDES

[75] Inventors: Gary P. Stack, Merion, Pa.; Magid A. Abou-Gharbia, Wilmington, Del.; Edward J. Podlesny, New Tripoli, Pa.

[73] Assignee: American Home Products Corporation, New York, N.Y.

[21] Appl. No.: 34,525

[22] Filed: Apr. 3, 1987

[51] Int. Cl.[4] .................. C07D 401/06; C07D 401/14; C07D 405/14; C07D 409/14

[52] U.S. Cl. ...................... 544/47; 544/105; 544/357; 544/362; 544/363; 544/360; 544/295

[58] Field of Search ............... 544/357, 362, 361, 363, 544/295, 331, 332, 105, 101, 47, 32, 360; 540/456, 457, 461, 463, 488, 490, 520

[56] References Cited

FOREIGN PATENT DOCUMENTS 2057845 6/1971 Fed. Rep. of Germany .
60-87262 5/1985 Japan .
7017031 11/1969 Netherlands .

OTHER PUBLICATIONS

Korgaonkar et al, J. Indian Chem. Soc., vol. LX, pp. 874–876 (1983).
Korgaonkar et al., Chemical Abstracts, vol. 101, entry 23432k (1984).

*Primary Examiner*—John M. Ford
*Attorney, Agent, or Firm*—Richard K. Jackson

[57] ABSTRACT

Substituted imides of the following formula are antipsychotic, anxiolytic agents with very little extrapyramidal side effects:

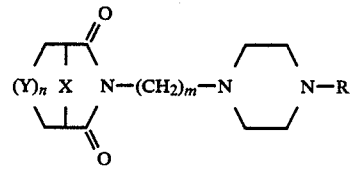

in which X is —O—, —S—, —SO—, —SO$_2$—, —CR$_3$R$_4$—where R$_3$ and R$_4$, independently, are hydrogen, alkyl of 1 to 4 carbon atoms or, taken together with the carbon atom to which they are attached, R$_3$ and R$_4$ form a cycloalkyl group of 3 to 5 carbon atoms; Y is alkylene of 1 to 3 carbon atoms or alkenylene of 2 to 3 carbon atoms; n is one of the integers 0 to 1; m is one of the integers 2, 3, 4 or 5; R is phenyl, halophenyl, trifluoromethylphenyl, alkoxyphenyl in which the alkoxy substituent contains 1 to 3 carbon atoms, 2-pyrimidinyl, halopyrimidin-2-yl, 2-pyrazinyl, halopyrazin-2-yl, 2-pyridinyl, cyanopyridin-2-yl, halopyridin-2-yl, quinolyl, or haloquinolyl; or a pharmaceutically acceptable salt thereof.

18 Claims, No Drawings

PSYCHOTROPIC BICYCLIC IMIDES

BACKGROUND OF THE INVENTION

Netherlands Pat. No. 7,017,031 discloses 8-(heteroarylpiperazinylalkyl)-8-azaspiro[4,5]decane-7,9-diones as tranquilizers and anti-emetics.

Japanese Pat. No. 60/87262 (C.A. 103: 215155K) discloses N-(heteroarylpiperazinylalkyl)cycloalkanosuccinimide derivatives as having anti-conflict activity.

DESCRIPTION OF THE INVENTION

In accordance with this invention there is provided a group of antipsychotic anxiolytic N-(aryl and heteroarylpiperazinylalkyl)bicyclic-1,3-dicarboxylic acid imides of the formula:

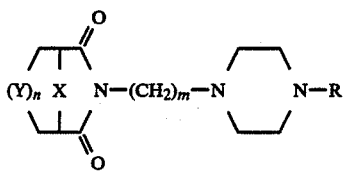

in which

X is —O—, —S—, —SO—, —SO$_2$—, CR$_3$R$_4$— where R$_3$ and R$_4$, independently, are hydrogen, alkyl of 1 to 4 carbon atoms or, taken together with the carbon atom to which they are attached, R$_3$ and R$_4$ form a cycloalkyl group of 3 to 5 carbon atoms;

Y is alkylene of 1 to 3 carbon atoms or alkenylene of 2 to 3 carbon atoms;

m is one of the integers, 2, 3, 4 or 5;

n is one of the integers 0 or 1;

R is phenyl, halophenyl, trifluoromethylphenyl, alkoxyphenyl in which the alkoxy substituent contains 1 to 3 carbon atoms, 2-pyrimidinyl, halopyrimidin-2-yl, 2-pyrazinyl, halopyrazin-2-yl, 2-pyridinyl, cyanopyridin-2-yl, halopyridin-2-yl, quinolyl, or haloquinolyl; or a pharmaceutically acceptable salt thereof.

Of the applicable halogen substituents present, including fluoro, chloro and bromo, chloro is preferred. The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The compounds of the invention are prepared by conventional methods. For example, a suitable cyclic 1,3-dicarboxylic acid, or the anhydride derived from it, is combined with the desired piperazinyl alkyl amine in a high boiling solvent such as toluene or xylene and refluxed for an extended period with either chemical (e.g. ethoxyacetylene) or mechanical (e.g. Dean-Stark trap) water removal, thusly:

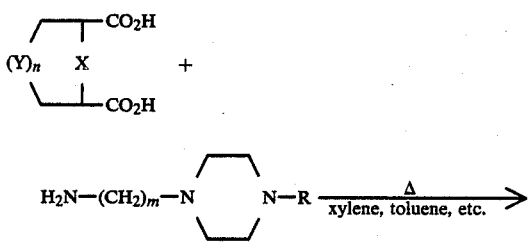

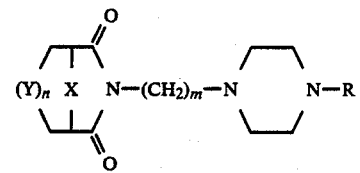

Alternatively, the compounds of this invention are readily prepared from the appropriate bicyclic imide via alkylation with a suitable dihalo lower alkane in the presence of a strong base such as sodium hydride, followed by reaction of the intermediate product with the desired aryl- or heteroaryl substituted piperazine, thusly:

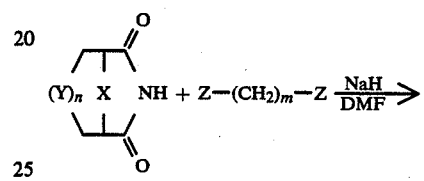

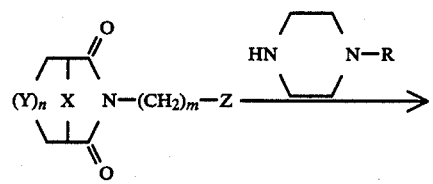

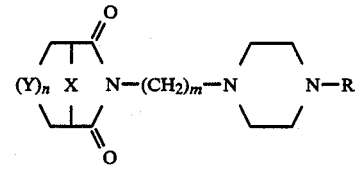

where Z represents —Cl or —Br.

An analogous preparation involves reaction of an N-protected piperazinyl alkylamine with the cyclic 1,3-dicarboxylic acid or anhydride followed by deprotection and N-substitution with the desired aryl or heteroaryl halide:

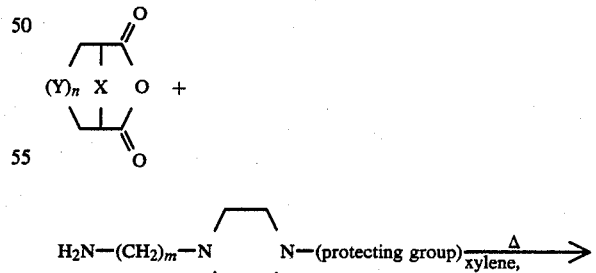

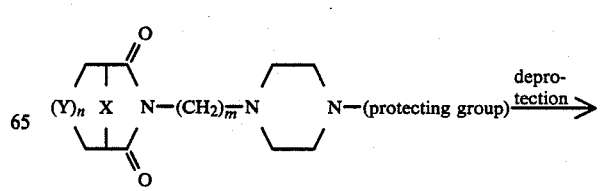

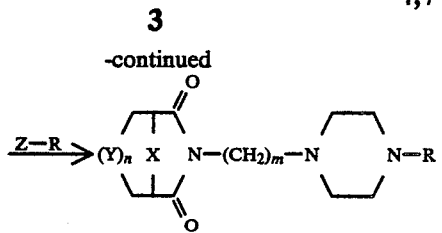

where the protecting group is any N-protecting group conventionally employed for that purpose, such as the benzyl group; deprotection is performed by hydrogenolysis in the presence of a noble metal catalyst such as platinum or palladium; and Z is chlorine, bromine or fluorine.

Similarly, the appropriate anhydride reacted with an omega hydroxy alkylamine, such as 4-aminobutanol, in the presence of bis(trimethylsilyl)acetamide, affords the dicarboxylic acid imide intermediate. Activation of the omega hydroxyl group, as with the mesyl group, followed by reaction with an N'-protected piperazine, such as 1-benzylpiperazine, affords the dicarboxylic-N-(N⁴-protected-piperazin-1-yl)alkyl imide. Removal of the N-protecting group followed by N-arylation, as with 2,6-dichloropyrazine, yields the desired compounds.

The antipsychotic properties of the compounds of this invention were established by standard pharmacologically accepted procedures involving conditioned avoidance studies in which trained male CD rats (Charles River), 400–450 g. body weight are exposed to a fifteen second warning tone (conditioned stimulus) continued for an additional fifteen seconds accompanied by electric shock. The rat can avoid the electric shock by jumping to an exposed shelf (shelf-jump response). A response during the initial warning tone is considered an avoidance response, while a response during shock delivery is considered as escape response. The shelf-jump response test procedure follows that of Herman et al., Comm. in Psychopharm., 3, pp. 165–171 (1979). The compounds of this invention were tested at a single dose (40 mg./kg. i.p.) in this procedure and were rated relative to their inhibition of conditioned avoidance responding. A similar test procedure (Discrete Trial) in which a lever press was substituted for a shelf-jump was used to establish the oral (p.o.) activity of the test compounds. Orally active compounds were tested over a full dose range and the Avoidance Block activities reported as "AB$_{50}$'s" (mg./kg.).

As a further measure of antipsychotic activity, the compounds of this invention were also studied as antagonists of apomorphine-induced stereotyped behavior and climbing wherein CF-1 mice (Charles River) receive the test compound i.p. at several dose levels (1, 10, 30 and 60 mg./kg.) (six mice per dose level) and thirty minutes later receive 1 mg./kg. apomorphine s.c. Five minutes after injection, the sniffing-licking-gnawing syndrome and climbing behavior induced by apomorphine are scored for each animal. Readings are repeated every five minutes during a thirty minute test session. An ED$_{50}$ value (with 95% confidence intervals) is calculated for inhibition of apomorphine-induced stereotyped behavior and climbing using a non-linear least squares calculation with inverse prediction. The ratio of the ED$_{50}$ for stereotyped behavior of the ED$_{50}$ for climbing is calculated. High ratios indicate antipsychotic activity with low liability for the extrapyramidal side effects which attend long term treatment with such standard antipsychotic drugs as haloperidol (ratio=1.00), chlorpromazine (ratio=1.51) and thioridazine (ratio=1.83).

In further support of the low potential for side-effects, the compounds of this invention were found to exhibit only weak binding to the D-2 dopamine receptor when tested in accordance with a modification of the procedure of Fields et al., Brain Res., 136, pp. 578–584 (1977) and Yamamura et al., eds., Neurotransmitter Receptor Binding, Raven Press, N.Y. (1978), wherein homogenized limbic brain tissue is incubated with ³H-spiroperidol and various concentrations of test compound, filtered and washed and shaken with Hydrofluor scintillation cocktail (National Diagnostics) and counted in a Packard 460CD scintillation counter. In those instances were moderate binding of the D-2 dopamine receptor occurred, the binding of those compounds at the 5HT$_{1A}$ serotonin receptor was sufficient to demonstrate useful selectivity of action of such magnitude as to relatively minimize any problem of extrapyramidal side effects. The results of this testing with compounds representative of the invention whose production is exemplified, infra, are as follows:

| | Conditioned Avoidance | | Apomorphine Antagonism ED$_{50}$, mg/kg, p.o. | | [³H] Spiroperidol Binding Inhibition Ki, |
| | Shelf-Jump 40 mg/kg, | Discrete Trial AB$_{50}$ | | | |
| Ex. | i.p. | p.o. | Stereotypy | Climbing | nM or % at 1 μM |
|---|---|---|---|---|---|
| 1 | ~80% | inactive | inactive | | 38% |
| 2 | >20% | weak | inactive | | 2,614 nM |
| 3 | ~80% | weak | inactive | | 44% |
| 4 | >20% | inactive | inactive | 53.27 | 12% |
| 5 | >20% | 47.31 | inactive | inactive | 27% |
| 6 | >20% | inactive | inactive | inactive | 14% |
| 7 | ~80% | 34.10 | inactive | | 21% |
| 8 | ~80% | 33.62 | inactive | 15.66 | 12% |
| 9 | >20% | 98.16 | inactive | 40.90 | 31% |
| 10 | ~80% | 7.03 | 4.98 | 1.05 | 80 nM |
| 11 | ~80% | 27.15 | 2.20 | 0.79 | 130 nM |
| 12 | >20% | weak | inactive | 51.65 | 7% |
| 13 | ~80% | 86.15 | inactive | 0.24 | 17% |
| 14 | >20% | 35.62 | inactive | >50 | 34% |
| 15 | ~80% | weak | inactive | >50 | 21% |
| 16 | ~80% | inactive | 54.14 | 9.17 | 12% |
| 17 | ~80% | 29.41 | 5.83 | 0.83 | 0% |
| 18 | >20% | inactive | inactive | 42.95 | 21% |
| 19 | ~80% | 27.02 | 30.99 | 9.06 | 97% |
| 20 | >20% | inactive | inactive | 0.20 | 53% |

| | Conditioned Avoidance | | Apomorphine Antagonism ED$_{50}$, mg/kg, p.o. | | [$^3$H] Spiroperidol Binding Inhibition Ki, |
|---|---|---|---|---|---|
| Ex. | Shelf-Jump 40 mg/kg, i.p. | Discrete Trial AB$_{50}$ p.o. | Stereotypy | Climbing | nM or % at 1 μM |
| 21 | >20% | inactive | inactive | 11.11 | 63% |
| 22 | ~80% | weak | 43.34 | 29.54 | 38% |

From these data, the activity profile of the compounds of this invention are seen to be that of antipsychotic agents with less potential for extra pyramidal side effects such as attend the use of major tranquillizers (sedation, pseudoparkinsonism, ataxia, muscle relaxation, etc.). This activity profile resembles that of the anxiolytic compound, buspirone. Further evidence that the pharmacological profile of the test compounds resembles that of buspirone was obtained by measuring the compound's ability to displace [$^3$H] 8-OH DPAT (dipropylaminotetralin) from the 5-HT$_{1A}$ serotonin receptor by the procedure of Hall et al., *J. Neurochem.* 44: 1685–1696, 1985. Compounds of the invention, like buspirone, exhibited potent affinity for this serotonin receptor subtype. The anxiolytic activity of buspirone is currently believed to be due, at least in part, to this receptor (Vander Maclen et al., *Eur. J. Pharmacol.* 1986, 129(1–2) 123–130. The test results of this study are as follows:

| Example | Inhibition of [$^3$H] 8-OH DPAT Binding Ki, nM or % at 1 μM |
|---|---|
| 1 | 10 nM |
| 2 | 106 nM |
| 3 | 31 nM |
| 4 | 46 nM |
| 5 | 16 nM |
| 6 | 90 nM |
| 7 | 31 nM |
| 8 | 68% |
| 9 | 60 nM |
| 10 | 3.61 nM |
| 11 | 3.89 nM |
| 12 | 54% |
| 13 | 122 nM |
| 14 | 35.2 nM |
| 15 | 63% |
| 16 | 129 nM |
| 17 | 5 nM |
| 18 | 76% |
| 19 | 15 nM |
| 20 | 16 nM |
| 21 | 15 nM |
| 22 | 4 nM |

Hence, the compounds of this invention are antipsychotic agents and anxiolytic agents useful in the treatment of psychoses such as paranoia and schizophrenia and in alleviating anxiety. As such, they may be administered neat or with a pharmaceutical carrier to a patient in need thereof. The pharmaceutical carrier may be solid or liquid.

A solid carrier can include one or more substances which may also act as flavoring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis or state of anxiety and the size, age and response pattern of the patient.

The following examples illustrate the production of representative compounds of this invention.

EXAMPLE 1

3-[4-[4-(2-Pyrimidinyl)-1-piperazinyl]butyl]-3-azabicyclo[3.3.1]nonane-2,4-dione 1,3-Cyclohexane dicarboxylic acid (4.0 g., 2.3 mmole) was converted to the anhydride by refluxing for three hours in 20 ml. of acetic anhydride. The excess acetic anhydride was removed under vacuum and the residue was extracted with hexane. Upon evaporation of the hexane yielded 3.54 g. of cyclohexane-1,3-dicarboxylic anhydride. This was combined with 5.99 g. (2.5 mmole) of 1-(4-aminobutyl)-4-(2-pyrimidinyl)piperazine in 50 ml. of dichloromethane and allowed to stir at room temperature overnight. The solvent was then removed in vacuo and replaced with 75 ml. of toluene. The mixture was refluxed for 24 hours with water separation via a Dean-Stark trap. The product was concentrated under vacuum and chromatographed on 200 g. of silica gel with 5% ethanol/chloroform. Recrystallization from 100 ml. of isopropanol by addition of 4.3 ml. of 4N HCl/isopropyl alcohol gave 2.06 g. of the title compound as the dihydrochloride; m.p. 213°–214.5° C.

Elemental Analysis: $C_{20}H_{29}N_5O_2.2HCl$. Calculated: C, 54.05; H, 7.03; N, 15.76. Found: C, 53.96; H, 6.79; N, 15.80.

EXAMPLE 2

3-[4-[4-(2-Pyrimidinyl)-1-piperazinyl]butyl]-3-azabicyclo[3.2.1]octane-2,4-dione 1,3-Cyclopentanedicarboxylic acid (4.0 g., 25 mmole) was converted to the anhydride by refluxing for 3 hours in 20 ml. of acetic anhydride. After removal of excess acetic anhydride, extraction with hexane and evaporation of the hexane, 3.95 g. of cyclopentane-1,3-dicarboxylic anhydride was obtained. The anhydride was combined with 6.51 g. (27 mmole) of 1-(4-aminobutyl)-4-(2-pyrimidinyl)piperazine in 50 ml. of dichloromethane and stirred at room temperature overnight. The dichloromethane was removed in vacuo and replaced with 75 ml. of toluene. The mixture was refluxed for 24 hours with water separation via a Dean-Stark trap. The product was concentrated under vacuum and chromatographed on 200 g. of silica gel with 5% ethanol/chloroform. The product-containing fractions were combined and concentrated and the residue crystallized (2 crops) from isopropanol with addition of 4N HCl/isopropanol. A second recrystallization from isopropanol gave 1.1 g. of the title compound as the dihydrochloride, hemihydrate; m.p. 201°–203° C.(d).

Elemental Analysis: $C_{19}H_{27}N_5O_2.2HCl.\frac{1}{2}H_2O$. Calculated: C, 51.94; H, 6.88; N, 15.94. Found: C, 51.97; H, 6.66; N, 15.93.

EXAMPLE 3

3-[4-[4-(2-Pyrimidinyl)-1-piperazinyl]butyl]-8-oxa-3-azabicyclo[3.2.1]octane-2,4-dione Tetrahydrofuran-2,5-dicarboxylic anhydride (1.5 g., 10 mmole) was dissolved in 150 ml. of toluene in a 500 ml. round bottom flask equipped with a Dean-Stark trap and condenser. 1-(4-Aminobutyl)-4-(2-pyrimidinyl)piperazine (2.59 g., 11 mmole) was added and the mixture was refluxed for 24 hours. When the analysis failed to detect the expected product, the solvent was removed in vacuum and replaced with xylene. Reflux was continued for 48 hours. The solvent was then removed in vacuum and the residue column chromatographed on 100 g. of silica gel using a gradient elution from pure chloroform to 5% ethanol/chloroform. The relevant fractions were combined and concentrated in vacuum and the product crystallized from isopropanol with the addition of 4N HCl/isopropanol. 1.2 Grams of the title compound was obtained as the dihydrochloride; m.p. 221°–222° C.

Elemental Analysis: $C_{18}H_{25}N_5O_3.2HCl$. Calculated: C, 50.00; H, 6.29; N, 16.20. Found: C, 49.85; H, 6.01; N, 16.07.

EXAMPLE 4

3-[4-[4-(2-Pyrimidinyl)-1-piperazinyl]butyl]-8-thia-3-azabicyclo[3.2.1]octane-2,4-dione Tetrahydrothiophene-2,5-dicarboxylic acid (3.0 g., 17 mmoles) was added to 200 ml. of benzene containing 1.5 g. (19 mmole) of acetyl chloride. The solution was refluxed for 4 hours and allowed to cool overnight. The solvent was then removed in vacuum and replaced with 250 ml. of xylene. 1-(4-Aminobutyl)-4-(2-pyrimidinyl)piperazine (4.4 g., 19 mmole) was added and the mixture refluxed for 48 hours. The solvent was again removed in vacuum and the residue was dissolved in chloroform and filtered through 75 g. of silica gel. After concentration in vacuum, the product was recrystallized from 25 ml. of isopropanol with addition of 4 ml. of 4N HCl/isopropanol. 1.1 Grams of the title compound was obtained as the hydrochloride, hemihydrate; m.p. 239°–241° C. (d).

Elemental Analysis: $C_{18}H_{25}N_5O_2S.HCl.\frac{1}{2}H_2O$. Calculated: C, 51.35; H, 6.46; N, 16.44. Found: C, 51.01; H, 6.17; N, 16.41.

EXAMPLE 5

3-[4-[4-(2-Pyrimidinyl)-1-piperazinyl]butyl]-9-thia-3-azabicyclo[3.3.1]nonane-2,4-dione Tetrahydrothiopyran-2,6-dicarboxylic anhydride (2.4 g., 14 mmole) and 1-(4-aminobutyl)-4-(2-pyrimidinyl)piperazine (3.5 g., 15 mmole) were dissolved in 250 ml. of toluene and refluxed for 48 hours with water removal via a Dean-Shark trap. The solvent was removed in vacuum and replaced with chloroform. The mixture was filtered through 75 g. of silica gel and concentrated in vacuum and the residue was crystallized from isopropanol with addition of 4N isopropanolic HCl. A second crystallization from isopropanol gave 1. g. of the title compound as the monohydrochloride; m.p. 238°–241° C. (d).

Elemental Analysis: $C_{19}H_{27}N_5O_2S.HCl$. Calculated: C, 53.57; H, 6.63; N, 16.44. Found: C, 53.42; H, 6.49; N, 16.40.

EXAMPLE 6

3-[4-[4-(2-Pyrimidinyl)-1-piperazinyl]butyl]-9-thia-3-azabicyclo[3.3.1]nonane-2,4-dione-9-oxide 3-[4-[4-(2-Pyrimidinyl)-1-piperazinyl]butyl]-9-thia-3-aza-bicyclo[3.3.1]nonane-2,4-dione hydrochloride (3.2 g., 8 mmole) prepared by the method of Example 5 was dissolved in 80 ml. of glacial acetic acid and 2.4 ml. of 30% hydrogen peroxide added. The mixture was stirred at room temperature overnight. It was then heated on the steam bath for 6 hours and again allowed to stand at room temperature overnight. The solvent was removed in vacuo and the residue filtered through silica gel in chloroform. After evaporation of the solvent and recrystallization from isopropanol with the addition of 4N HCl/isopropyl alcohol, 0.82 g. of the title compound was obtained as the hydrochloride; m.p. 254°–257° C.

Elemental Analysis: C$_{19}$H$_{27}$N$_5$O$_3$S.HCl. Calculated: C, 51.63; H, 6.38; N, 15.85. Found: C, 51.35; H, 6.29; N, 15.43.

EXAMPLE 7

2-[4-[4-(6-Chloro-2-pyrazinyl)-1-piperazinyl]butyl]-3-azabicyclo[3.3.1]nonane-2,4-dione Cyclohexane-1,3-dicarboxylic anhydride (2.3 g., 15 mmole) and 1-(4-aminobutyl)-4-(6-chloro-2-pyrazinyl)piperazine (4.0 g., 15 mmole) were combined in 300 ml. of xylene and refluxed for 48 hours with water separation via a Dean-Stark trap. The reaction was cooled and filtered through 75 g. of silica gel using 2% ethanol/CHCl$_3$ to rinse the column. The solvent was removed in vacuum and the residue recrystallized from isopropanol with addition of 4N isopropanolic HCl to give 2.3 g. of the title compound as the monohydrochloride; m.p. 238°–239° C.

Elemental Analysis: C$_{20}$H$_{28}$N$_2$O$_2$Cl.HCl. Calculated: C, 54.30; H, 6.61; N, 15.83. Found: C, 54.13; H, 6.30; N, 15.69.

EXAMPLE 8

3-[4-[4-(6-Chloro-2-pyrazinyl)-1-piperazinyl]butyl]-3-azabicyclo[3.2.1]octane-2,4-dione 1,3-Cyclopentane dicarboxylic acid (8.0 g., 51 mmole) was converted to the anhydride by refluxing for 3 hours in 100 ml. of acetic anhydride. The excess solvent was removed under vacuum and the residue was stored in vacuum for 18 hours. The crude anhydride thus obtained was combined with 14 g. (50 mmole) of 1-(4-aminobutyl)-4-benzylpiperazine hydrochloride and 5.0 g. (50 mmole) of triethylamine in 500 ml. of xylene. The mixture was refluxed for 48 hours with water separation via a Dean-Stark trap. The product was concentrated under vacuum and chromatographed on 200 g. of silica gel with 2% ethanol/chloroform. The product was crystallized from ethanol by addition of 4N HCl/isopropyl alcohol to obtain cyclopentane-1,3-dicarboxylic-N-[4-(4-benzyl-1-piperazinyl)butyl]imide dihydrochloride; m.p. 273°–275° C.

5.6 Grams (13 mmole) of the benzyl protected intermediate prepared in the preceding paragraph was dissolved in 100 ml. of acetic acid and 1.0 g. of 10% palladium on carbon added. The mixture was hydrogenated at 60 psi for 24 hours, filtered through celite, concentrated in vacuum, and crystallized from ethanol. 4.9 Grams of the product, cyclopentane-1,3-dicarboxylic-N-[4-(1-piperazinyl)butyl]imide was recovered as the dihydrochloride, hemihydrate; m.p. 240°–241° C.

To 1.05 g. (3.0 mmole) of the deprotected intermediate prepared in the preceding paragraph was added 0.60 g. (4.0 mmole) of 2,6-dichloropyrazine, 1.0 g. (10 mmole) of triethylamine and 50 ml. of dimethylformamide. The mixture was heated at 60° C. for 16 hours. The solvent was removed in vacuum and replaced with 250 ml. of dichloromethane. The solution was washed with saturated bicarbonate solution, saturated brine and dried over sodium sulfate. Concentration in vacuum and crystallization from isopropanol with the addition of 4N HCl/isopropyl alcohol gave 0.54 g. of the title compound as the hydrochloride, hemihydrate; m.p. 220°–221° C.

Elemental Analysis: C$_{19}$H$_{26}$N$_5$O$_2$Cl.HCl.½H$_2$O. Calculated: C, 52.17; H, 6.45; N, 16.01. Found: C, 52.15; H, 6.14; N, 16.45.

EXAMPLE 9

3-[4-[4-(2-Quinolyl)-1-piperazinyl]butyl]-3-azabicyclo[3.2.1]octane-2,4-dione 1,3-Cyclopentane dicarboxylic acid (1.6 g., 10 mmole) and 1-(4-aminobutyl)-4-(2-quinolyl)piperazine (2.8 g., 10 mmole) were combined in 200 ml. of xylene and refluxed for 24 hours with water removal via a Dean-Stark trap. The solvent was then removed in vacuum and the residue redissolved in chloroform and filtered through 75 g. of silica gel. The column was rinsed with 5% ethanol/chloroform and the product-containing fractions were combined and evaporated. The residue was recrystallized from isopropanol with the addition of 4N isopropanolic HCl to give 820 mg. of the title compound as the dihydrochloride hemihydrate; m.p. 240°–242° C.

Elemental Analysis: C$_{24}$H$_{30}$N$_4$O$_2$.2HCl.½H$_2$O. Calculated: C, 59.02; H, 6.81; N, 11.47. Found: C, 58.93; H, 6.59; N, 11.35.

EXAMPLE 10

3-[4-[4-[3-(Trifluoromethyl)phenyl]-1-piperazinyl]butyl]-3-azabicyclo[3.2.1]octane-2,4-dione 1,3-Cyclopentane dicarboxylic anhydride (2.2 g., 15 mmole) and 1-(4-aminobutyl)-4-[3-(trifluoromethyl)phenyl]piperazine (4.5 g., 15 mmole) were combined in 300 ml. of methylene chloride and stirred for 30 minutes at room temperature. The solvent was replaced with 200 ml. of xylene and the mixture was refluxed for 48 hours with water removal via a Dean-Stark trap. The solvent was removed in vacuum and the residue filtered through 75 g. of silica gel with 2% ethanol/chloroform as eluent. The product was concentrated in vacuum and crystallized from 50 ml. of isopropanol with the addition of 5 ml. of 4N isopropanolic HCl. A second recrystallization from ethanol gave 2.7 g. of the title compound as the hydrochloride, quarter hydrate; m.p. 208°–209° C.

Elemental Analysis: C$_{22}$H$_{25}$N$_3$O$_2$F$_3$.HCl.¼H$_2$O. Calculated: C, 56.89; H, 6.40; N, 9.05. Found: C, 56.92; H, 6.26; N, 8.95.

EXAMPLE 11

3-[4-[4-(3-Chlorophenyl)-1-piperazinyl]butyl]-3-azabicyclo[3.2.1]octane-2,4-dione 1,3-Cyclopentane dicarboxylic anhydride (2.2 g., 15 mmole) and 4.0 g. (15 mmole) of 1-(4-aminobutyl)-4-(3-chlorophenyl)piperazine were combined in 300 ml. of methylene chloride and stirred for 30 minutes at room temperature. The solvent was replaced with xylene and the mixture was refluxed for 48 hours with water removal via a Dean-Stark trap. The solvent was removed in vacuum and the residue filtered through 75 g. of silica gel with 2% ethanol/chloroform as eluent. The product was concentrated in vacuum and crystallized from 50 ml. of isopropanol with addition of 4N isopropanolic HCl. Recrystallization from ethanol gave 1.6 g. of the title compound as the hydrochloride, quarter hydrate; m.p. 199°–202° C.

Elemental Analysis: C$_{21}$H$_{28}$N$_3$O$_2$Cl.HCl.¼H$_2$O. Calculated: C, 58.54; H, 6.90; N, 9.75. Found: C, 58.38; H, 6.73; N, 9.24.

EXAMPLE 12

3-[4-[4-(6-Chloro-2-pyrazinyl)-1-piperazinyl]butyl]-8-oxa-3-azabicyclo[3.2.1]octane-2,4-dione Tetrahydrofuran-2,5-dicarboxylic anhydride (1.26 g., 8.8 mmole) and 1-(4-aminobutyl)-4-(6-chloro-2-pyrazinyl)piperazine (2.37 g., 8.8 mmole) were combined and stirred for 30 minutes in 200 ml. of methylene chloride. The solvent was removed in vacuum and replaced with 300 ml. of xylene. The mixture as refluxed for 48 hours with water removal via a Dean-Stark trap. After cooling, the mixture was filtered through 75 g. of silica gel and the column rinsed with 5% ethanol/chloroform. The product was concentrated in vacuum and recrystallized from isopropanol with addition of 4N isopropanolic HCl. 0.60 Grams of the title compound was obtained as the monohydrochloride; m.p. 233°-235° C. (d).

Elemental Analysis: $C_{18}H_{24}N_5O_3Cl.HCl$. Calculated: C, 50.24; H, 5.85; N, 16.28. Found: C, 49.89; H, 5.83; N, 16.06.

EXAMPLE 13

3-[4-[4-(2-Pyrimidinyl)-1-piperazinyl]butyl]-9-oxa-3-azabicyclo[3.3.1]nonane-2,4-dione Tetrahydropyran-2,6-dicarboxylic anhydride (3.0 g., 19 mmole) and 1-(4-aminobutyl)-4-(2-pyrimidinyl)piperazine (4.98 g., 21 mmole) were combined and stirred for 30 minutes in 200 ml. of methylene chloride. The solvent was removed in vacuum and replaced with 300 ml. of xylene. The mixture was refluxed for 48 hours with water removal via a Dean-Stark trap. The solvent was again removed in vacuum and the residue was column chromatographed on 100 g. of silica with a gradient elution beginning with chloroform and ending with 5% ethanol in chloroform. The relevant fractions were combined and evaporated and the product crystallized from isopropanol with the addition of 4N isopropanolic HCl and ether. A second crystallization from isopropanol gave 1.9 g. of the title compound as the dihydrochloride, hemihydrate; m.p. 232°-233° C. (d).

Elemental Analysis: $C_{19}H_{27}N_5O_3.2HCl.\frac{1}{2}H_2O$. Calculated: C, 50.11; H, 6.64; N, 15.38. Found: C, 50.41; H, 6.76; N, 15.07.

EXAMPLE 14

3-[4-[4-(6-Chloro-2-pyrazinyl)-1-piperazinyl]butyl]-9-thia-3-azabicyclo[3.3.1]nonane-2,4-dione Tetrahydrothiopyran-2,6-dicarboxylic anhydride (3.7 g., 21 mmole) and 1-(4-aminobutyl)-4-(6-chloro-2-pyrazinyl)piperazine (5.63 g., 21 mmole) were combined in 200 ml. of methylene chloride and stirred for 30 minutes at room temperature. The solvent was removed in vacuum and 200 ml. of toluene added. The mixture was refluxed for 48 hours with water removal via a Dean-Stark trap. Upon cooling, the reaction was concentrated to an oil and this was dissolved in 2% ethanol/chloroform and filtered through silica gel. The fractions which contained the product were concentrated in vacuum and the resulting residue was recrystallized from isopropyl alcohol with the addition of 4N isopropanolic HCl. 0.6 Grams of the title compound was obtained as the hydrochloride, hydrate; m.p. 248°-250° C.

Elemental Analysis: $C_{19}H_{26}N_5O_2Cl.HCl.H_2O$. Calculated: C, 47.69; H, 6.11; N, 14.64. Found: C, 47.59; H, 5.78 N, 14.64.

EXAMPLE 15

3-[4-[4-(6-Chloro-2-pyrazinyl)-1-piperazinyl]butyl]-9-oxa-3-azabicyclo[3.3.1]nonane-2,4-dione Tetrahydropyran-2,6-dicarboxylic anhydride (3.12 g., 20 mmole) and 1-(4-aminobutyl)-4-(6-chloro-2-pyrazinyl)piperazine (5.94 g., 22 mmole) were combined in 200 ml. of methylene chloride and stirred for 30 minutes at room temperature. The solvent was removed in vacuum and replaced with 350 ml. of xylene. The mixture was refluxed for 50 hours with water removal via a Dean-Stark trap. The xylene was evaporated and the residue was filtered through 75 g. of silica gel with 2% ethanol/chloroform. The product was concentrated in vacuum and crystallized from isopropanol with the addition of 4N isopropanolic HCl. A second recrystallization from methanol gave 4.18 g. of the title compound as the monohydrochloride; m.p. 252°-253° C.

Elemental Analysis: $C_{19}H_{26}N_5O_3Cl.HCl$. Calculated: C, 51.35; H, 6.12; N, 15.76. Found: C, 51.21; H, 6.02; N, 15.56.

EXAMPLE 16

3-[4-[4-(2-Pyrazinyl)-1-piperazinyl]butyl]-3-azabicyclo[3.3.1]nonane-2,4-dione 1,3-Cyclohexane dicarboxylic acid (1.65 g., 9.6 mmole) was dissolved in 75 ml. of acetic anhydride and refluxed for 3 hours under $N_2$. The solvent was removed in vacuum and replaced with 250 ml. of methylene chloride. 1-(4-Aminobutyl)-4-(2-pyrazinyl)piperazine (2.35 g., 10 mmole) was added and the mixture was stirred for 30 minutes at room temperature. The solvent was then replaced with 200 ml. xylene and the mixture was refluxed for 24 hours with water removal via a Dean-Stark trap. The product was concentrated to an oil in vacuum and column chromatographed in 100 g. silica gel with a gradient elution proceeding from methylene chloride to 5% isopropanol/methylene chloride. Evaporation of the relevant fractions gave 1.4 g. of the title compound, which was recrystallized from isopropanol with the addition of 4N isopropanolic HCl to give 900 mg. of monohydrochloride monohydrate; m.p. 226°-229° C.

Elemental Analysis: $C_{20}H_{29}N_5O_2.HCl.H_2O$. Calculated: C, 56.39; H, 7.57; N, 16.44. Found: C, 56.57; H, 7.12; N, 16.86.

EXAMPLE 17

3-[4-[4-(2-Methoxyphenyl)-1-piperazinyl]butyl]-3-azabicyclo[3.2.1]octane-2,4-dione 1,3-Cyclopentane dicarboxylic acid (2.4 g., 15 mmole) was treated at reflux with 100 ml. of acetic anhydride for 3 hours. The anhydride thus formed was concentrated and stored in vacuum. It was combined with 4.0 g. (15 mmole) of 1-(4-aminobutyl)-4-(2-methoxyphenyl)piperazine in 300 ml. of xylene and refluxed for 48 hours with water removal via a Dean-Stark trap. The reaction was allowed to cool and filtered through 75 g. of silica gel using 2% ethanol in chloroform as eluent. Concentration in vacuum and recrystallization from 75 ml. of isopropanol with addition of 4N isopropanolic HCl gave 3.5 g. of the title compound as the dihydrochloride; m.p. 215.5°–216.5° C.

Elemental Analysis: $C_{22}H_{31}N_3O_3.2HCl$. Calculated: C, 57.64; H, 7.26; N, 9.17. Found: C, 57.41; H, 7.41; N, 9.13.

EXAMPLE 18

3-[4-[4-(6-Chloro-2-pyrazinyl)-1-piperazinyl]butyl]-8,8-dimethyl-3-azabicyclo[3.2.1]octane-2,4-dione 2,2-Dimethylcyclopentane-1,3-dicarboxylic anhydride (1.68 g., 10 mmole) and 1-(4-aminobutyl)-4-(6-chloro-2-pyrazinyl)piperazine (2.97 g., 11 mmole) were combined in 500 ml. of xylene and refluxed for 48 hours with Dean-Stark water removal. Concentration in vacuum, column chromatography on 100 g. of silica gel with chloroform, and recrystallization from 50 ml. of isopropanol with addition of 4N isopropanolic HCl gave 0.55 g. of the title compound as the monohydrochloride; m.p. 210° C. (d).

Elemental Analysis: $C_{21}H_{30}N_5O_2Cl.HCl$. Calculated: C, 55.26; H, 6.85; N, 15.34. Found: C, 55.30; H, 6.84; N, 14.95.

EXAMPLE 19

3-[4-[4-[3-(Trifluoromethyl)phenyl]-1-piperazinyl]butyl]-9-oxa-3-azabicyclo[3.3.1]nonane-2,4-dione 2,6-Tetrahydropyrandicarboxylic acid (3.7 g., 21 mmole) was dissolved in 100 ml. of anhydrous ether and treated with 4 ml. of trifluoroacetic anhydride for 2.5 hours at room temperature. Concentration in vacuum and Kugelrohr distillation gave 3.14 g. of anhydride.

1-(4-aminobutyl)-4-[3-(trifluoromethyl)phenyl]piperazine (3.01 g., 10 mmole) and 1.56 g. (10 mmole) of the above anhydride were combined in 500 ml. of xylene and refluxed for 48 hours with water removal via a Dean-Stark trap. The solvent was removed in vacuum and the residue column chromatographed on 100 g. silica gel with 2% ethanol/chloroform. The product-containing fractions were combined and evaporated and the residue recrystallized from 75 ml. of isopropanol with the addition of 2.5 ml. of 4N isopropanolic HCl. 1.6 Grams of the title compound was obtained as the monohydrochloride; m.p. 200°–201.5° C.

Elemental Analysis: $C_{22}H_{28}N_3O_3F_3$. Calculated: C, 55.52; H, 6.14; N, 8.83. Found: C, 55.49; H, 6.12; N, 8.89.

EXAMPLE 20

3-[4-[4-(2-Pyrimidinyl)-1-piperazinyl]butyl]-8,8-dimethyl-3-azabicyclo[3.2.1]octane-2,4-dione 2,2-Dimethylcyclopentane-1,3-dicarboxylic anhydride (1.68 g., 10 mmole) and 1-(4-aminobutyl)-4-(2-pyrimidinyl)piperazine (2.55 g., 11 mmole) were combined in 500 ml. of xylene and refluxed for 48 hours with water removal via a Dean-Stark trap. The solvent was removed in vacuo and the residue column chromatographed on 100 g. of silica gel using a gradient elution from straight chloroform to 5% ethanol/chloroform. Concentration of the product in vacuum and recrystallization from isopropanol with addition of 4N isopropanolic HCl and acetone gave 600 mg. of the title compound as the dihydrochloride, monohydrate; m.p. 227°–229° C. (d).

Elemental Analysis: $C_{21}H_{31}N_5O_2.2HCl.H_2O$. Calculated: C, 52.93; H, 7.40; N, 14.70. Found: C, 52.96; H, 7.10; N, 15.25.

EXAMPLE 21

8-[4-[4-(2-Pyrimidinyl)-1-piperazinyl]butyl]-8-azabicyclo[4.3.1]dec-3-ene-7,9-dione 5-Cycloheptane-1,3-dicarboxylic anhydride (2.1 g., 13 mmole) and 1-(4-aminobutyl)-4-(2-pyrimidinyl)piperazine (3.27 g., 14 mmole) were combined in 500 ml. of xylene and refluxed for 48 hours with Dean-Stark water removal. The solvent was removed in vacuum and the residue column chromatographed on 100 g. of silica gel with chloroform. After concentration in vacuum, the residue was recrystallized from isopropanol with the addition of 4N isopropanolic HCl to give 0.6 g. of the title compound as the dihydrochloride, quarter hydrate; m.p. 236°–238° C. (d).

Elemental Analysis: $C_{21}H_{29}N_5O_2.2HCl.\frac{1}{4}H_2O$. Calculated: C, 54.72; H, 6.89; N, 15.19. Found: C, 54.60; H, 6.70; N, 15.43.

EXAMPLE 22

3-[3-[4-[3-(Trifluoromethyl)phenyl]-1-piperazinyl]propyl]-3-azabicyclo[3.2.1]octane-2,4-dione 3-Azabicyclo[3.2.1]octane-2,4-dione (3.1 g., 20 mmole) was dissolved in 100 ml. of dimethylformamide and 1.0 g. (25 mmole) of 60% sodium hydride/mineral oil dispersion was added. After 30 minutes at room temperature, 6.4 g. (40 mmole) of 1-bromo-3-chloropropane was added and the mixture heated at 80° C. under $N_2$ for 24 hours. The solvent was then removed in vacuum and the residue column chromatographed on 100 g. of silica gel with methylene chloride as eluent. The intermediate thus obtained was combined with 4.6 g. (20 mmole) of 1-[3-(trifluoromethyl)phenyl]piperazine, 2.0 g. (20 mmole) of triethylamine and 6.0 g. (40 mmole) of sodium iodide in 200 ml. of DMF and heated at 60° C. for 24 hours. The solvent was removed in vacuum and replaced with 500 ml. of methylene chloride. This was washed with 200 ml. portions of saturated aqueous sodium bicarbonate, water, and saturated brine and dried over sodium sulfate. After filtration and concentration in vacuum, the product was dissolved in chloroform, filtered through 75 g. of silica gel, concentrated and recrystallized from isopropanol with the addition of 4N isopropanolic HCl to give 2.7 g. of monohydrochloride; m.p. 219°–220° C.

Elemental Analysis: $C_{21}H_{26}N_3O_2F_3.HCl$. Calculated: C, 56.56; H, 6.10; N, 9.42. Found: C, 56.25; H, 6.09; N, 9.35.

What is claimed is:

1. A compound of the formula:

$$(Y)_n \begin{array}{c} O \\ \diagup \diagdown \\ X \quad N-(CH_2)_m-N \quad N-R \\ \diagdown \diagup \\ O \end{array}$$

in which
X is —O—, —S—, —SO—, —SO$_2$—, CR$_3$R$_4$— where R$_3$ and R$_4$, independently, are hydrogen, alkyl of 1 to 4 carbon atoms or, taken together with the carbon atom to which they are attached, R$_3$ and R$_4$ form a cycloalkyl group of 3 to 5 carbon atoms;
Y is alkylene of 1 to 3 carbon atoms or alkenylene of 2 to 3 carbon atoms;

m is one of the integers, 2, 3, 4, or 5;

n is one of the integers 0 or 1; and

R is 2-pyrimidinyl, halopyrimidin-2-yl, 2-pyrazinyl, halopyrazin-2-yl, 2-pyridinyl, cyanopyridin-2-yl, halopyridin-2-yl, quinolyl, or haloquinolyl;

or a pharmaceutically acceptable salt thereof.

2. A compound of claim 1 which is 3-[4-[4-(2-pyrimidinyl)-1-piperazinyl]butyl]-3-azabicyclo[3.3.1]nonane-2,4-dione, or a pharmaceutically acceptable salt thereof.

3. A compound of claim 1 which is 3-[4-[4-(2-pyrimidinyl)-1-piperazinyl]butyl]-3-azabicyclo[3.2.1]octane-2,4-dione, or a pharmaceutically acceptable salt thereof.

4. A compound of claim 1 which is 3-[4-[4-(2-pyrimidinyl)-1-piperazinyl]butyl]-8-oxa-3-azabicyclo[3.2.1]octane-2,4-dione, or a pharmaceutically acceptable salt thereof.

5. A compound of claim 1 which is 3-[4-[4-(2-pyrimidinyl)-1-piperazinyl]butyl]-8-thia-3-azabicyclo[3.2.1]octane-2,4-dione, or a pharmaceutically acceptable salt thereof.

6. A compound of claim 1 which is 3-[4-[4-(2-pyrimidinyl)-1-piperazinyl]butyl]-9-thia-3-azabicyclo[3.3.1]nonane-2,4-dione, or a pharmaceutically acceptable salt thereof.

7. A compound of claim 1 which is 3-[4-[4-(2-pyrimidinyl-1-piperazinyl]butyl]-9-thia-3-azabicyclo[3.3.1]nonane-2,4-dione-9-oxide, or a pharmaceutically acceptable salt thereof.

8. A compound of claim 1 which is 2-[4-[4-(6-chloro-2-pyrazinyl)-1-piperazinyl]butyl]-3-azabicyclo[3.3.1]nonane-2,4-dione, or a pharmaceutically acceptable salt thereof.

9. A compound of claim 1 which is 3-[4-[4-(6-chloro-2-pyrazinyl)-1-piperazinyl]butyl]-3-azabicyclo[3.2.1]octane-2,4-dione, or a pharmaceutically acceptable salt thereof.

10. A compound of claim 1 which is 3-[4-[4-(2-quinolyl)-1-piperazinyl]butyl]-3-azabicyclo[3.2.1]octane-2,4-dione, or a pharmaceutically acceptable salt thereof.

11. A compound of claim 1 which is 3-[4-[4-(6-chloro-2-pyrazinyl)-1-piperazinyl]butyl]-8-oxa-3-azabicyclo[3.2.1]octane-2,4-dione, or a pharmaceutically acceptable salt thereof.

12. A compound of claim 1 which is 3-[4-[4-(2-pyrimidinyl)-1-piperazinyl]butyl]-9-oxa-3-azabicyclo[3.3.1]nonane-2,4-dione, or a pharmaceutically acceptable salt thereof.

13. A compound of claim 1 which is 3-[4-[4-(6-chloro-2-pyrazinyl)-1-piperazinyl]butyl]-9-thia-3-azabicyclo[3.3.1]nonane-2,4-dione, or a pharmaceutically acceptable salt thereof.

14. A compound of claim 1 which is 3-[4-[4-(6-chloro-2-pyrazinyl)-1-piperazinyl]butyl]-9-oxa-3-azabicyclo[3.3.1]nonane-2,4-dione, or a pharmaceutically acceptable salt thereof.

15. A compound of claim 1 which is 3-[4-[4-(2-pyrazinyl)-1-piperazinyl]butyl]-3-azabicyclo[3.3.1]nonane-2,4-dione, or a pharmaceutically acceptable salt thereof.

16. A compound of claim 1 which is 3-[4-[4-(6-chloro-2-pyrazinyl)-1-piperazinyl]butyl]-8,8-dimethyl-3-azabicyclo[3.2.1]octane-2,4-dione, or a pharmaceutically acceptable salt thereof.

17. A compound of claim 1 which is 3-[4-[4-(2-pyrimidinyl)-1-piperazinyl]butyl]-8,8-dimethyl-3-azabicyclo[3.2.1]octane-2,4-dione, or a pharmaceutically acceptable salt thereof.

18. A compound of claim 1 which is 8-[4-[4-(2-pyrimidinyl)-1-piperazinyl]butyl]-8-azabicyclo[4.3.1]-dec-3-ene-7,9-dione, or a pharmaceutically acceptable salt thereof.

* * * * *